United States Patent [19]

Brennan et al.

[11] 4,304,871

[45] Dec. 8, 1981

[54] CONVERSION OF SYNTHESIS GAS TO HYDROCARBON MIXTURES UTILIZING A DUAL CATALYST BED

[75] Inventors: James A. Brennan, Cherry Hill; Philip D. Caesar, West Deptford; Julius Ciric, Pitman; William E. Garwood, Haddonfield, all of N.J.

[73] Assignee: Mobil Oil Corporation, New York, N.Y.

[21] Appl. No.: 825,875

[22] Filed: Aug. 19, 1977

Related U.S. Application Data

[63] Continuation-in-part of Ser. No. 793,016, May 2, 1977, abandoned, and Ser. No. 729,938, Oct. 10, 1976, abandoned, which is a continuation of Ser. No. 566,167, Apr. 8, 1975, abandoned, said Ser. No. 793,016, is a continuation-in-part of Ser. No. 729,938, , and Ser. No. 732,834, Oct. 15, 1976, abandoned, which is a continuation-in-part of Ser. No. 583,353, Jun. 2, 1975, abandoned, and Ser. No. 566,167, , abandoned.

[51] Int. Cl.$^3$ .................................................. C07C 1/04
[52] U.S. Cl. ................................... 518/717; 518/715; 252/455 Z
[58] Field of Search ............... 260/449.6 R, 449.6 M, 260/449 R, 449 M, 676, 673, 668, 673.5, 450; 518/717, 715

[56] References Cited

U.S. PATENT DOCUMENTS

| | | | |
|---|---|---|---|
| 3,756,942 | 9/1973 | Cattanach | 260/673 |
| 3,760,024 | 9/1973 | Catlanach | 260/673 |
| 3,894,102 | 7/1975 | Chang et al. | 260/449 R X |
| 3,894,106 | 7/1975 | Chang et al. | 260/673 |
| 3,960,978 | 6/1976 | Givens | 260/673 |
| 3,972,958 | 8/1976 | Garwood et al. | 260/449.6 R X |
| 4,041,094 | 8/1977 | Kuo et al. | 260/449 R X |
| 4,046,830 | 9/1977 | Kuo | 260/449 R X |

FOREIGN PATENT DOCUMENTS

828228 10/1975 Belgium .............................. 260/449

*Primary Examiner*—Howard T. Mars
*Attorney, Agent, or Firm*—Charles A. Huggett; Michael G. Gilman; Charles J. Speciale

[57] ABSTRACT

A gaseous mixture of carbon monoxide and hydrogen is passed in contact over a first catalyst bed comprising an iron or cobalt containing Fischer-Tropsch catalyst in combination with a crystalline aluminosilicate of the class of crystalline zeolite represented by ZSM-5 so as to obtain a liquid hydrocarbon product having a boiling range of less than 400° F. at a 90% overhead and being a predominantly olefinic product. The total products from said contact including said liquid hydrocarbon product are then converted over a second catalyst bed containing HZSM-5 to obtain a highly aromatic product, i.e., greater than 20 weight percent.

10 Claims, No Drawings

CONVERSION OF SYNTHESIS GAS TO HYDROCARBON MIXTURES UTILIZING A DUAL CATALYST BED

RELATION TO OTHER APPLICATIONS

This application is a continuation-in-part of applications Ser. No. 729,938, filed Oct. 10, 1976, and Ser. No. 793,016, filed May 2, 1977. Application Ser. No. 793,106 is a continuation-in-part of U.S. patent application Ser. No. 732,834, filed Oct. 15, 1976, and Ser. No. 729,938, filed Oct. 10, 1976. Ser. No. 732,834 is, in turn, a continuation-in-part of U.S. patent application Ser. No. 566,167, filed Apr. 8, 1975, and Ser. No. 583,353, filed June 2, 1975. Application Ser. No. 729,938 is a continuation of U.S. patent application Ser. No. 566,167, filed Apr. 8, 1975, all abandoned.

BACKGROUND OF THE INVENTION

1. Field of the Invention

This invention is concerned with an improved process for converting synthesis gas, i.e., mixtures of gaseous carbon oxides with hydrogen or hydrogen donors, to hydrocarbon mixtures. In one aspect, this invention is particularly concerned with a process for converting synthesis gas substantially directly to hydrocarbon mixtures rich in aromatics.

2. Prior Art

Processes for the conversion of coal and other hydrocarbons such as natural gas to a gaseous mixture consisting essentially of hydrogen and carbon monoxide, or of hydrogen and carbon dioxide, or of hydrogen and carbon monoxide and carbon dioxide, are well known. An excellent summary of the art of gas manufacture, including synthesis gas, from solid and liquid fuels, is given in *Encyclopedia of Chemical Technology*, Edited by Kirk-Othmer, Second Edition, Volume 10, pages 353–433, (1966), Interscience Publishers, New York, New York, the contents of which are incorporated herein by reference. The technique for gasification of coal or other solid, liquid or gaseous fuel are not considered to be a part of this invention.

It is well known that synthesis gas comprising carbon monoxide and hydrogen will undergo conversion to form reduction products of carbon monoxide, at temperatures in the range of 300° F. to about 850° F. and pressures in the range of one to one thousand atmospheres pressure, over a fairly wide variety of catalysts. The Fischer-Tropsch process, for example, which has been extensively studied, produces a range of hydrocarbons, waxy materials and some liquid materials which have been used as low octane gasoline. The types of catalysts that have been studied for this and related processes include those based on metals or oxides of iron, cobalt, nickel, ruthenium, thorium, rhodium and osmium.

The range of catalysts and catalyst modifications disclosed in the art encompass an equally wide range of conversion conditions for the reduction of carbon monoxide by hydrogen and provide considerable flexibility toward obtaining selected boiling-range products. Nonetheless, in spite of this flexibility, it has not been possible heretofore to provide a catalyst for medium pressure operation (5-30 atm) which will produce particularly olefin compositions comprising primarily beta double bond characteristics and boiling in the gasoline boiling range. A review of the status of this art is given in "Carbon Monoxide-Hydrogen Reactions," *Encyclopedia of Chemical Technology*, Edited by Kirk-Othmer, Second Edition, Volume 4, pp. 446–488, Interscience Publishers, New York, New York.

It has been discovered that synthesis gas may be converted to oxygenated organic compounds and these compounds then converted to higher hydrocarbons, particularly high octane gasoline, by contacting synthesis gas with a carbon monoxide reduction catalyst followed by contacting the conversion products so produced with a special type of zeolite catalyst in a separate reaction zone. This two-stage conversion is described in copending U.S. patent application Ser. No. 387,220, filed Aug. 9, 1973. Compositions of iron, cobalt or nickel deposited in the inner absorption regions of crystalline zeolites are described in U.S. Pat. No. 3,013,990. Attempts to convert synthesis gas over X-zeolite base exchanged with iron, cobalt and nickel are described in Erdol and Kohle-Erdgas, Petrochemie; Brennstoff-Chemie, Vol. 25, No. 4, pp. 187–188, April 1972.

In copending application Ser. No. 733,982, filed Oct. 20, 1976, there is disclosed a process for the conversion of syngas to various hydrocarbon products utilizing an intimate mixture of a Fischer-Tropsch component and a ZSM-5 type zeolite. The process of said copending application is a one-stage process and among the hydrocarbons that can be produced are those which are rich in aromatics.

Although the process of this copending application is indeed effective in producing products having a substantial quantity of aromatics, nevertheless, there are disadvantages associated with said process, primarily in the regeneration aspect of the catalyst. It is known that when processes of this type are operated under conditions which favor the production of aromatics that there is also produced substantial amounts of coke which are deposited about the acid ZSM-5 catalyst. This requires that the catalyst be subjected to frequent regeneration, and due to the fact that the process of said copending application Ser. No. 733,982 involved a catalyst mixture containing a Fischer-Tropsch component such as an iron catalyst and a ZSM-5 catalyst, the extent and amount of regeneration was limited by the effect that the regeneration would have on the iron component. Thus, although HZSM-5 by itself exhibits a remarkable stability with regard to regeneration of the same by burning off carbon deposits, the same is not true with respect to a Fischer-Tropsch catalyst, in general, and iron and cobalt containing catalysts in particular.

It is also to be understood that another difficulty in the area of regeneration stems from the fact that those conditions which are optimum for the regeneration of an acidic catalyst such as ZSM-5 are not necessarily optimum for the regeneration of a Fischer-Tropsch component. Other difficulties which are experienced in a one-stage process involving the production of aromatics are due to the nature of the chemistry which is involved. Thus, for example, in order to produce aromatics a ZSM-5 type zeolite has to "work harder" than it would if an olefinic product were desired. Thus, a greater degree of severity with regard to reaction conditions is required for the production of aromatics than would be required for the production of olefins. As has heretofore been stated, the production of aromatics also deposits more coke on the catalyst such that it deactivates faster than would be the case if an olefinic product were produced. Thus, it can be seen in those situations where an intimate mixture of an iron or cobalt containing Fischer-Tropsch component and a ZSM-5 zeolite were used to convert syngas, the catalyst would have to be regenerated more frequently when aromatic hydrocarbons were produced. This in turn would further complicate the situation since as has heretofore been stated the conditions for the regeneration of the Fischer-Tropsch component are not necessarily the conditions required for the regeneration of the zeolite component.

Additionally, while not wishing to be bound by any theory of operation, it nevertheless appears that the cleaner the feed material is to a ZSM-5 type zeolite, the longer that it will last in converting said feed to aromatics.

BRIEF SUMMARY OF THE INVENTION

It has now been discovered that high aromatic, high octane gasoline can be produced by reacting synthesis gas, i.e. mixtures of hydrogen gas with gaseous carbon oxide or the equivalents of such mixtures utilizing a dual bed conversion process. In the first bed, the syngas mixture is reacted over a mixture of either an iron or cobalt containing catalyst and a ZSM-5 type zeolite in such a way so as to balance the activity of the ZSM-5 type zeolite with the iron or cobalt containing Fischer-Tropsch component and to produce a liquid olefinic naphtha having a boiling range of less than 400° F. at 90% overhead with an aromatic content of less than about 20 weight percent and an olefin plus aromatic content of at least 50 weight percent wherein the olefins are predominantly branched chain. The product from this first stage conversion, without any separation of intermediates, is thereafter processed in a second stage or second bed with an acidic zeolite such as HZSM-5. It is apparent from the above description of the novel process of this invention that the first stage is, in essence, the type of operation disclosed and claimed in copending Ser. Nos. 793,015 and 793,016, the entire disclosure of both applications being incorporated by reference. The second stage of the novel process of this invention would reside in contacting the product from the first stage without any separation of intermediates over a second bed which would contain a zeolite such as HZSM-5 which would be operated under aromatization conditions so as to effect conversion of the products of the first stage into a high octane, high aromatic gasoline.

The process of this invention allows for a considerably greater flexibility with respect to the regeneration of the catalyst since the dual beds can be regenerated separately such that the process is capable of being operated at longer cycle times. As pointed out earlier, the coke which is deposited during the aromatizing reaction is deposited on the acidic zeolite, and in the novel process of this invention, this zeolite is remarkably stable during many regeneration cycles. On the other hand, the first stage operation is carried out such that coke formation is not excessive due to the fact that aromatization conditions are avoided.

DETAILED DESCRIPTION AND PREFERRED EMBODIMENTS

Synthesis gas as used in this invention consists of a mixture of hydrogen gas with gaseous carbon oxides including carbon monoxide and carbon dioxide. By way of illustration, a typical purified synthesis gas will have the composition, on a water-free basis, in volume percentages, as follows: hydrogen, 51; carbon monoxide, 40; carbon dioxide, 4; methane, 1; and nitrogen, 4.

The synthesis gas may be prepared from fossil fuels by any of the known methods, including such in situ gasification processes as the underground partial combustion of coal and petroleum deposits. The term fossil fuels, as used herein, is intended to include anthracite and bituminous coal, lignite, crude petroleum, shale oil, oil from tar sands, natural gas, as well as fuels derived from simple physical separations or more profound transformations of these materials, including coked coal, petroleum coke, gas oil, residua from petroleum distillation, and two or more of any of the foregoing materials in combination. Other carbonaceous fuels such as peat, wood and cellulosic waste materials also may be used.

The raw synthesis gas produced from fossil fuels will contain various impurities such as particulates, sulfur, and metal carbonyl compounds, and will be characterized by a hydrogen-to-carbon oxides ratio which will depend on the fossil fuel and the particular gasification technology utilized. In general, it is desirable for the efficiency of subsequent conversion steps to purify the raw synthesis gas by the removal of impurities. Techniques for such purification are known and are not part of this invention. However, it may not be necessary to remove substantially all the sulfur impurities when thoria is used as the carbon monoxide reducing component, since thoria is relatively little affected by sulfur compounds. Furthermore, should it be required, it is preferred to adjust the hydrogen-to-carbon oxides volume ratio to be within the range of from 0.2 to 6.0 prior to use in this invention. Should the purified synthesis gas be excessively rich in carbon oxides, it may be brought within the preferred range by the well known water-gas shift reaction. On the other hand, should the synthesis gas be excessively rich in hydrogen, it may be adjusted into the preferred range by the addition of carbon dioxide or carbon monoxide. Purified synthesis gas adjusted to contain a volume ratio of hydrogen-to-carbon oxides of from 0.2 to 6.0 will be referred to as adjusted synthesis gas.

It is contemplated that the synthesis gas for use in this invention includes art-recognized equivalents to the already-described mixtures of hydrogen gas with gaseous carbon oxides. Mixtures of carbon monoxide and steam, for example, or of carbon dioxide and hydrogen, to provide adjusted synthesis gas by in situ reaction, are contemplated.

The catalysts employed in the first bed of this invention comprise two different catalytic components. One component is selected from the class of iron or cobalt containing Fischer-Tropsch catalysts and the other component is initially a crystalline aluminosilicate characterized by a pore dimension greater than about 5 Angstroms, a silica-to-alumina ratio of at least 12 and which has had its catalytic activity balanced with the iron and cobalt in order to form the liquid olefinic naphtha previously described.

The crystalline zeolite component used in the first bed is initially selected from the class of crystalline zeolites represented by ZSM-5.

In the first bed, the crystalline zeolite is provided as the major component of the heterogenous catalyst mixture with the carbon monoxide reducing component comprising a minor component on a volume basis of the catalyst mixture.

The iron or cobalt containing component characterized by catalytic activity for the reduction of carbon monoxide may be selected from substantially any of the art-recognized catalysts for producing hydrocarbon, oxygenated products, or mixtures thereof, from synthesis gas. However, a potassium promoted iron, Fe(K) is preferred.

This invention includes the use of chemical and structural promoters. These promoters include copper, chromia, alumina, the alkaline earths, the rare earths, and alkali. Alkali, e.g., the carbonates of Group IA of the Periodic Table, and especially potassium, is of particular importance for use as promoters with iron catalysts. Potassium modified iron Fischer-Tropsch catalyst greatly reduces the conversion to methane. Supports such as kieselguhr sometimes act beneficially.

The iron or cobalt containing carbon monoxide reducing component may be furnished as elemental metal or as a corresponding metal compound. Frequently in the preparation and use of such catalytic substances there will be one or more partial or complete transformations from the elemental metal to the compound, or vice versa. By way of illustration, pure iron, roasted in an oxygen atmosphere in the presence of added aluminum and potassium nitrates provides a composition that contains 97% $Fe_3O_4$, 2.4% $Al_2O_3$, and 0.6% $K_2O$ with trace amounts of sulfur and carbon.

The crystalline aluminosilicate component of the first bed catalyst arrangement is characterized initially and before reducing or eliminating the acid activity by a pore dimension greater than about 5 Angstroms, i.e. it is capable of sorbing paraffins, and it has a silica-to-alumina ratio of at least 12 and a constraint index within the range of 1 to 12. Zeolite A, for example, with a silica-to-alumina ratio of 2.0 is not useful in this invention, and it has no pore dimension greater than about 5 Angstroms.

The crystalline aluminosilicates herein referred to, also known as zeolites, constitute an unusual class of natural and synthetic minerals. They are characterized by having a rigid crystalline framework structure composed of an assembly of silicon and aluminum atoms, each surrounded by a tetrahedron of shared oxygen atoms, and a precisely defined pore structure. Exchangeable cations are present in the pores.

The zeolites utilized herein exhibit some unusual properties. They are very active even with silica to alumina ratios exceeding 30. This activity is surprising since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from, the intra-crystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful in this invention have a silica to alumina ratio of at least about 12 and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The zeolites useful as catalysts in this invention freely sorb normal hexane and have a pore dimension greater than about 5 Angstroms. In addition, their structure must provide constrained access to some larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is substantially excluded and the zeolite is not of the desired type. Zeolites with windows of 10-membered rings are preferred, although excessive puckering or pore blockage may render these zeolites substantially ineffective. Zeolites with windows of twelve-membered rings do not generally appear to offer sufficient constraint to produce the advantageous conversions desired in the instant invention, although structures can be conceived, due to pore blockage or other cause, that may be operative.

Rather than attempt to judge from crystal structure whether or not a zeolite possesses the necessary constrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

Constraint Index =

$$\frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those which employ a zeolite having a constraint index from 1.0 to 12.0. Constraint Index (CI) values for some typical zeolites including some not within the scope of this invention are:

| CAS | C.I. |
|---|---|
| Erionite | 38 |
| ZSM-5 | 8.3 |
| ZSM-11 | 8.7 |
| ZSM-35 | 6.0 |
| TMA Offretite | 3.7 |
| ZSM-38 | 2.0 |
| ZSM-12 | 2 |
| Beta | 0.6 |
| ZSM-4 | 0.5 |
| Acid Mordenite | 0.5 |
| REY | 0.4 |
| Amorphous Silica-alumina | 0.6 |

The above-described Constraint Index is an important, and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint Index seems to vary somewhat with severity of operation (conversion). Therefore, it will be appreciated that it may be possible to so select test conditions to establish multiple constraint indexes for a particular given zeolite which may be both inside and outside the above defined range of 1 to 12.

Thus, it should be understood that the parameter and property "Constraint Index" as such value is used herein is an inclusive rather than an exclusive value. That is, a zeolite when tested by any combination of conditions within the testing definition set forth hereinabove to have a constraint index of 1 to 12 is intended to be included in the instant catalyst definition regardless that the same identical zeolite tested under other defined conditions may give a constraint index value outside of 1 to 12.

The class of zeolites defined herein is exemplified by ZSM-5, ZSM-11, ZSM-12, ZSM-21, and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

U.S. application Ser. No. 358,192, filed May 7, 1973, the entire contents of which are incorporated herein by reference, describes a zeolite composition, and a method of making such, designated as ZSM-21 which is useful in this invention. Recent evidence has been adduced which suggests that this composition may be composed of at least two (2) different zeolites, designated ZSM-35 and ZSM-38, one or both of which are the effective material insofar as the catalysis of this invention is concerned. Either or all of these zeolites is considered to be within the scope of this invention. ZSM-5 is described in U.S. application Ser. No. 528,061, filed Nov. 29, 1974. ZSM-38 is described in U.S. application Ser. No. 528,060, filed Dec. 29, 1974.

The specific zeolites described, when prepared in the presence of organic cations, are substantially catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this special type zeolite, however, the presence of these cations does appear to favor the formation of this special type of zeolite. More generally, it is desirable to activate this type zeolite by base exchange with ammonium salts followed by calcination in air at about 1000° F. for from about 15 minutes to about 24 hours.

Natural zeolites may sometimes be converted to this type zeolite by various activation procedures and other treatments such as base exchange, steaming, alumina extraction and calcination, alone or in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12 and ZSM-21, with ZSM-5 particularly preferred.

In a preferred aspect of this invention, the initial zeolites useful as catalysts herein are selected as those having a crystal framework density, in the dry hydrogen form, of not substantially below about 1.6 grams per cubic centimeter. It has been found that zeolites which satisfy all three of these criteria are most desired. Therefore, the preferred catalysts of this invention are those comprising zeolites having a constraint index as defined above of about 1 to 12, a silica to alumina ratio of at least about 12 and a dried crystal density of not substantially less than about 1.6 grams per cubic centimeter. The dry density for known structures may be calculated from the number of silicon plus aluminum atoms per 1000 cubic Angstroms, as given e.g. on page 19 of the article on "Zeolite Structure" by W. M. Meier. This paper, the entire contents of which are incorporated herein by reference, is included in "Proceedings of the Conference on Molecular Sieves, London, April, 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, seems to be important as the locus of the catalytic activity.

Crystal framework densities of some typical zeolites including some which are not within the purview of this invention are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

As has been previously set forth, this invention resides in the production of a particular liquid product utilizing a catalyst mixture comprised of an iron or cobalt Fischer-Tropsch component and a ZSM-5 type component in a first bed and thereafter passing the total effluent from said first bed over a second bed containing a hydrogen or ammonium exchanged ZSM-5 type zeolite. The catalyst mixtures used in the first bed may be prepared in various ways. The two components may be separately prepared in the form of catalyst particles such as pellets or extrudates, for example, and then mixed in the required proportions. The particle size of the individual component particles may be quite small, for example, from about 0.01 to about 300 microns, when intended for use in fluid bed operation; or they may be as large as up to about ½ inch for fixed bed operation. The two components may also be mixed as powders in desired proportions and formed into pellets or extrudate, each pellet containing both components in substantially the required proportions. Binders such as clays may be added to the mixture. Alternatively, the component that has catalytic activity for the reduction of carbon monoxide may be formed on the acidic crystalline aluminosilicate component by conventional means such as impregnation of that solid with salt solutions of the desired metals, followed by drying and calcination. Base exchange of the acidic crystalline aluminosilicate component also may be used in some selected cases to effect the introduction of part or all of the carbon monoxide reduction component. Other means for forming the intimate mixture may be used, such as: precipitation of the carbon monoxide reduction component in the presence of the acidic crystalline aluminosilicate; or electrolytic deposition of metal on the zeolite, or deposition of metal from the vapor phase. Various combinations of the above preparative methods will be obvious to those skilled in the art of catalyst preparation.

In copending application Ser. No. 729,938, filed Oct. 6, 1976, it is demonstrated that for the production of aromatic gasoline from synthesis gas the iron catalyst component is preferably retained in an arrangement wherein it is surrounded by a relatively large proportion of crystalline zeolite component. The same type of configuration is preferred in this invention, particularly under fixed bed operating conditions. The crystalline zeolite-containing component, modified as herein provided, is so arranged to statistically promote the sequential reaction mechanism of synthesis gas conversion to primarily olefin intermediates by the iron catalyst followed by chain growth of the olefin intermediate with the modified zeolite catalyst component to form branched chain and internal olefins in preference to aromatics and before the olefin intermediate has a chance to contact additional particles of iron catalyst. Thus, the abundance of zeolite particles about the iron particle intercepts the olefin intermediate of iron catalyst conversion before the olefin intermediate can build up into long-chain linear wax molecules. Supporting evidence for the above-identified reaction sequence and catalyst component arrangement promoting the scavenging function by the zeolite catalyst component is provided by related studies on propylene or methanol conversion to form aromatics with a ZSM-5 crystalline zeolite. The fact that the zeolite component provides a scavenging function when properly proportioned with respect to the carbon monoxide reducing component is further supported by data obtained with the heterogenous catalyst mixture after treatment of particularly the zeolite component to substantially eliminate the aromatizing function.

An analysis of an iron Fischer-Tropsch synthesis catalyst used in obtaining the data of this invention is as follows:

| | |
|---|---|
| FeO | 24.5 |
| $Fe_2O_3$ | 69.1 |
| $Al_2O_3$ | 2.5 |
| $K_2O$ | 0.8 |
| CaO | 2.0 |
| $SiO_2$ | 0.4 |

While not wishing to be bound by any theory of operation, nevertheless, it appears that in the novel process of this invention, all that is required from the Fischer-Tropsch portion of the catalyst is that it be capable of converting the syngas to an olefinic product at a minimum temperature of at least 450° F. and more desirably, at least 550° F. up to a maximum temperature of 750° F. such that no more than about 30 weight percent of methane plus ethane is formed. The exact temperatures will vary depending on whether an iron or cobalt catalyst is used as will be hereinafter set forth.

Thus, it can be seen that the novel process of this invention does not have the same constraints with respect to the use of Fischer-Tropsch catalyst as existed in heretofore practiced prior art processes. The entire function of the Fischer-Tropsch catalyst in the novel catalyst combination of this invention is merely to produce light olefinic and/or oxygenated hydrocarbons from syngas at good yields and selectivity. The particular nature of the intermediate olefins or oxygenated hydrocarbons produced really does not matter too much, since the zeolite can act on this material and transform it to the particular olefinic gasoline with which the novel process of this invention is concerned.

Although there are many factors which can be taken into consideration when one is discussing the severity of a reaction, nevertheless, by far the most important parameter is the temperature. Thus, once a particular form of cobalt or iron-containing Fischer-Tropsch catalyst is chosen to meet the above set forth criterion, the optimum temperature range of the reaction is thus fixed. Although the particular temperature will vary depending upon the particular form of the Fischer-Tropsch catalyst component which is employed, the simple fact remains that for any given Fischer-Tropsch component, the specific temperature which will cause syngas to react to form a predominantly olefinic product and produce no more than 30 weight percent of methane plus ethane is easily determined.

Thus, it is known in the Fischer-Tropsch art that certain iron catalysts are more active than others. For example, a precipitated iron catalyst referred to in the literature is more active than the commercial fused-magnetite potassium promoted ammonia synthesis catalyst, FeK. Thus, the temperatures which can be used with the more active iron Fischer-Tropsch catalysts are lower than those which can be used with the less active Fischer-Tropsch catalysts—all other considerations being equal.

It then becomes necessary, in the course of the novel process of this invention, to balance the activity of the zeolite component utilized in the catalyst composition, such that it will be able to function within the preset optimum temperature range determined by the iron Fischer-Tropsch component and produce the desired products. It is known in the art that the aromatization activity of the acid form of a ZSM-5 crystalline zeolite can be reduced by cationic substitution, by raising its silica-to-alumina ratio, by steam, by addition of phosphoric compounds, etc. Another way of reducing the activity of the zeolite is to dilute it with inorganic type materials, such as alumina, silica-alumina, clay, etc. This has the effect of increasing the space velocity of the feed with respect to the zeolitic component such that the severity of the reaction is reduced. Conversely, the activity of the zeolite can be increased by increasing the volume ratio of acidic component with respect to the iron Fischer-Tropsch component. This, in effect, lowers the space velocity of the feed with respect to the zeolitic component. It also increases the probability that light α-olefin intermediates will be intercepted by the zeolite and converted to internal olefins.

Although there are many factors which can be taken into consideration when one is discussing the severity of a reaction, nevertheless, by far the most important parameter is the temperature. Thus, once a particular form of cobalt Fischer-Tropsch catalyst is chosen to meet the above set forth criterion, the optimum temperature range of the reaction is thus fixed. Although the particular temperature will vary depending upon the particular form of cobalt Fischer-Tropsch catalyst component which is employed, the simple fact remains that for any given cobalt Fischer-Tropsch component, the specific temperature which will cause syngas to react to form a predominantly olefinic product and produce no more than 30 weight percent of methane plus ethane is easily determined.

It then becomes necessary, in the course of the novel process of this invention, to balance the activity of the zeolite component utilized in the catalyst composition, such that it will be able to function within the preset optimum temperature range determined by the cobalt Fischer-Tropsch component and produce the desired products. It is known in the art that the aromatization activity of a ZSM-5 crystalline zeolite can be reduced by cationic substitution, by raising its silica-to-alumina ratio, by steam, by addition of phosphoric compounds, etc. Another way of reducing the activity of the zeolite is to dilute it with inorganic type materials, such as alumina, silica-alumina, clay, etc. This has the effect of increasing the space velocity of the feed with respect to the zeolitic component such that the severity of the reaction is reduced. Conversely, the activity of the zeolite can be increased by increasing the volume ratio of acidic component with respect to the cobalt Fischer-Tropsch component. This, in effect, lowers the space velocity of the feed with respect to the zeolitic component. It also increases the probability that light alpha-olefin intermediates will be intercepted by the zeolite and converted to internal olefins.

Thus, for example, if the effective range of a cobalt-containing Fischer-Tropsch catalyst for converting syngas to light alpha-olefins lies between 450°–550° F., then the most active form of HZSM-5 type zeolite is required to trap and convert those light olefins to branched and internal olefins. However, if the cobalt-containing catalyst is effective at 550°–650° F., then a potassium or otherwise partially deactivated form of ZSM-5 should be used to prevent excessive aromatics formation.

The first bed or stage of this invention is carried out at temperatures ranging from about 450° F. and more preferably at least 550° F. to about 750° F. when an iron containing component is used and from 450° to 650° F. and preferably 470°–540° F. when a cobalt containing component is used. The first bed reactor is carried out at gas hourly space velocities (GHSV) ranging from 500 to 20,000 and more desirably from 1000 to 6000 based on fresh feed and total catalyst volume. Hydrogen to carbon oxides ratios can vary from 0.5 to 6.0 and more preferably from 1.0 to 2.0, pressures ranging from 50 to 1000 psig and more preferably from 150 to 400 psig. The ratio of the Fischer-Tropsch component to the acidic solid (zeolite plus binder) is not narrowly critical and can range from 1.0 to a practical maximum of 20 volumes of the acidic solid per volume of the Fischer-Tropsch component. A particularly desirable range is from 2 to 10 volumes of acidic solid per volume of Fischer-Tropsch component.

Operating within the above referred-to parameters will result in a process wherein at least 50% of the carbon monoxide in the fresh feed is actually converted. Since theoretical conversions vary with syngas composition, a preferred conversion range on the fresh feed is at least 50% of the carbon monoxide and of the hydrogen based on theoretical.

The catalyst which is utilized in the second bed or second stage in the novel process of this invention can be best described as the same zeolite utilized in the first stage with the exception that its aromatizing activity has not been reduced. The ZSM-5 type zeolites utilized in the second stage are usually base exchanged with ammonium ions, hydrogen ions or a mixture of the two either alone or with stabilizing cations such as rare earths. A particularly preferred embodiment with respect to the second stage catalyst is HZSM-5. The zeolite in the second stage can be utilized per se or can be admixed with a suitable inorganic binder such as alumina.

It is to be understood that although this invention has been described with respect to separate beds or separate stages that it is possible to carry out both the first stage and second stage operation in separate reactors, as well as in the same reactor, i.e. cascading the products from the first stage into a second bed within the same reactor.

Although the second stage operation can be carried out at the same conditions as the first stage operation, nevertheless, this is not an absolute requirement, as is obvious when separate reactors are employed. In any event, suitable second stage operating conditions include temperatures ranging from 550°–800° F. and more preferably from 550°–650° F.; suitable operating pressures include 50 to 1000, and more preferably from 200 to 600 psig.

It is to be noted that gas hourly space velocities (GHSV) ranging from 500 to 20,000 and more particularly from 1000 to 6000 are suitable.

The following examples will illustrate the novel process of this invention.

EXAMPLES 1 & 2

0.4 cc of 14–25 mesh Fe(K) mixed with 1.6 cc of KZSM-5 extrudate (0.95 wt% K) were placed in a first bed of a two-bed reactor. Two cc of 12–25 mesh quartz were placed below the first bed separated by a screen. Below the quartz in a second bed were placed 2 cc of 12–25 mesh HZSM-5.

A charge of syngas consisting of a mixture of hydrogen and carbon monoxide in a 2:1 volume ratio was introduced into the first bed and converted. The effluent from the first bed, without any separation, was then further converted in the second bed.

In the above experiments, one heating block gave a common temperature control for both beds.

Two experiments were carried out at about 3300 GHSV, 200 psig and 600° F. in order to check reproducibility with the following results:

| | | |
|---|---|---|
| CO Conversion, Wt % | 96 | 97 |
| $H_2$ Conversion, Wt % | 54 | 54 |

| % Wt % Converted to: | | |
|---|---|---|
| $CO_2$ | 32 | 31 |
| Hydrocarbon | 68 | 69 |
| Hydrocarbon Composition, Wt % | | |
| $C_1$ | 16 | 18 |
| $C_2$ | 4 | 5 |
| $C_3$ | 8 | 7 |
| $C_4$ | 19 | 19 |
| $C_5$ | 12 | 12 |
| $C_6+$ | 41 | 39 |
| | 100 | 100 |
| Aromatics in $C_6+$, Wt % | 57 | 58 |

EXAMPLE 3

The process of Example 2 was repeated with the exception that the initial temperature was 575° F. and it was raised to 600° F. after 7 days on stream. Results are shown in the following table.

TABLE

| Temperature Setting, °F. | ← | ← | ←575 | → | → | → | ← | ← | →600 | → | → | → |
|---|---|---|---|---|---|---|---|---|---|---|---|---|
| Run Accum. Time, Days | 1.0 | 2.0 | 3.9 | 4.9 | 5.9 | 6.9 | 7.9 | 8.9 | 9.9 | 10.9 | 11.9 | 12.9 |
| GHSV (Based on Top Bed) | ← | ← | ← | ← | ←3285 | → | → | → | → | → | → | → |
| Temp., Top, Average, °F. | 598 | 599 | 601 | 599 | 599 | 597 | 620 | 623 | 625 | 619 | 618 | 621 |
| Bottom, Average, | 579 | 579 | 580 | 579 | 580 | 578 | 599 | 599 | 601 | 599 | 599 | 601 |
| CO Conversion, Wt % | 97 | 97 | 96 | 96 | 95 | 93 | 95 | 94 | 94 | 94 | 95 | 96 |
| $H_2$ Conversion, Wt % | 56 | 55 | 53 | 52 | 51 | 51 | 52 | 52 | 51 | 49 | 52 | 52 |
| % Wt C Converted to: | | | | | | | | | | | | |
| $CO_2$ | 33 | 33 | 34 | 35 | 35 | 35 | 34 | 34 | 35 | 35 | 35 | 34 |
| Hydrocarbon | 67 | 67 | 66 | 65 | 65 | 65 | 66 | 66 | 65 | 65 | 65 | 66 |
| Reactor Effluent, Wt % | | | | | | | | | | | | |
| HC | 28.6 | 28.4 | 27.4 | 26.8 | 26.1 | 25.7 | 26.3 | 26.7 | 26.6 | 25.8 | 26.9 | 27.3 |
| $H_2O$ | 19.9 | 19.8 | 18.8 | 17.8 | 17.7 | 17.4 | 19.0 | 18.1 | 17.7 | 18.0 | 17.5 | 17.1 |
| $CO_2$ | 43.6 | 43.8 | 44.5 | 45.7 | 45.0 | 45.6 | 44.5 | 45.2 | 45.0 | 44.4 | 45.4 | 45.0 |
| CO | 2.3 | 2.3 | 3.3 | 3.7 | 5.0 | 4.9 | 4.2 | 3.9 | 4.7 | 5.7 | 4.1 | 4.3 |
| $H_2$ | 5.6 | 5.7 | 6.0 | 6.0 | 6.2 | 6.4 | 6.0 | 6.1 | 6.0 | 6.1 | 6.1 | 6.3 |
| Hydrocarbon Composition, Wt % | | | | | | | | | | | | |
| $C_1$ | 16 | 17 | 17 | 18 | 18 | 18 | 21 | 21 | 21 | 21 | 21 | 21 |
| $C_2$ | 4 | 4 | 5 | 5 | 6 | 6 | 7 | 6 | 6 | 7 | 7 | 7 |
| $C_3$ | 8 | 7 | 6 | 5 | 5 | 5 | 5 | 5 | 6 | 6 | 6 | 6 |
| $C_4$ | 17 | 14 | 12 | 11 | 10 | 9 | 9 | 11 | 11 | 10 | 11 | 12 |
| $C_5$ | 13 | 12 | 12 | 12 | 10 | 10 | 12 | 11 | 16 | 11 | 10 | 11 |
| $C_6+$ | 42 | 46 | 48 | 49 | 51 | 52 | 46 | 46 | 46 | 45 | 45 | 43 |
| Olefins in $C_5$, Wt % | 3 | 6 | 18 | 25 | 31 | 39 | 26 | 26 | 34 | 38 | 40 | 40 |
| $C_5$ Olefin Distribution, Wt % | | | | | | | | | | | | |
| $C_5=1$ | — | 3 | 3 | 3 | 3 | 2 | 3 | 3 | 3 | 3 | 2 | 2 |
| $2M1C_4=$ | — | 18 | 18 | 18 | 18 | 19 | 19 | 19 | 19 | 19 | 18 | 19 |
| $3M1C_4=$ | — | 2 | 2 | 2 | 2 | 2 | 2 | 2 | 2 | 2 | 2 | 2 |
| $T2C_5=$ | — | 11 | 12 | 12 | 12 | 12 | 12 | 12 | 12 | 12 | 13 | 13 |
| $C2C_5=$ | — | 6 | 6 | 6 | 6 | 6 | 6 | 6 | 6 | 6 | 6 | 6 |
| $2M2C_4+$ | — | 60 | 59 | 59 | 59 | 59 | 58 | 58 | 58 | 58 | 59 | 58 |
| $C_6+$ Aromatics, Wt % | 53 | 47 | 32 | 26 | 23 | 19 | 29 | 27 | 23 | 20 | 21 | 20 |
| Liq. Prod. 90% Pt., °F.(D-2887) | 364 | 364 | 367 | — | — | — | 369 | — | — | — | — | — |

The coke content of the bottom bed (i.e. HZSM-5) after 13 days was 18.6 wt%, accounting for the decrease in aromatics.

EXAMPLE 4

The process of Example 3 was repeated with the exception that no ZSM-5 was used in the first stage. The first stage catalyst consisted of 0.4 cc (1.03 grams) of FeK mixed with 1.6 cc (0.94 grams) of gamma alumina. The second stage catalyst was the same as in Example 3. The results are shown in the following table.

TABLE

| Temperature Setting, °F. | ← | ← | 575 | → | → | ← | 600 | → |
|---|---|---|---|---|---|---|---|---|
| Run Accum. Time, Days | .8 | 1.8 | 2.9 | 4.7 | 6.9 | 8.9 | 11.5 | 12.4 |
| GHSV (Based on Top Bed) | ← | ← | ← | 3280 | → | → | → | → |
| Temp., Top, Average, °F. | 589 | 591 | 591 | 592 | 590 | 613 | 615 | 614 |
| Bottom, Average | 576 | 577 | 577 | 577 | 577 | 599 | 598 | 598 |
| CO Conversion, Wt % | 98 | 97 | 96 | 92 | 91 | 89 | 84 | 82 |
| $H_2$ Conversion, Wt % | 50 | 50 | 44 | 42 | 41 | 41 | 35 | 32 |

TABLE-continued

| % Wt C Converted to: | | | | | | | | |
|---|---|---|---|---|---|---|---|---|
| $CO_2$ | 29 | 30 | 33 | 32 | 33 | 32 | 34 | 36 |
| Hydrocarbon | 71 | 70 | 67 | 68 | 67 | 68 | 66 | 64 |
| Reactor Effluent, Wt % | | | | | | | | |
| HC | 30.5 | 30.4 | 28.9 | 26.6 | 26.2 | 25.8 | 24.3 | 22.8 |
| $H_2O$ | 22.4 | 21.3 | 17.2 | 18.6 | 16.2 | 17.5 | 14.2 | 12.1 |
| $CO_2$ | 38.6 | 39.4 | 43.3 | 40.4 | 41.8 | 39.3 | 39.6 | 40.4 |
| CO | 2.2 | 2.6 | 3.6 | 7.2 | 8.3 | 10.0 | 13.7 | 16.1 |
| $H_2$ | 6.3 | 6.3 | 7.0 | 7.2 | 7.5 | 7.4 | 8.2 | 8.6 |
| Hydrocarbon Composition, Wt % | | | | | | | | |
| $C_1$ | 16 | 17 | 19 | 17 | 18 | 18 | 19 | 21 |
| $C_2$ | 3 | 4 | 5 | 7 | 8 | 7 | 8 | 9 |
| $C_3$ | 7 | 6 | 5 | 5 | 5 | 6 | 6 | 7 |
| $C_4$ | 16 | 13 | 10 | 11 | 12 | 13 | 14 | 14 |
| $C_5$ | 13 | 13 | 14 | 15 | 16 | 15 | 16 | 15 |
| $C_6+$ | 45 | 47 | 47 | 45 | 41 | 41 | 37 | 34 |
| Olefins in $C_5$, Wt % | 8 | 29 | 50 | 66 | 72 | 71 | 77 | 79 |
| $C_5$ Olefin Distribution, Wt % | | | | | | | | |
| $C_5= 1$ | 2 | 2 | 2 | 2 | 2 | 3 | 2 | 2 |
| $2M1C_4=$ | 18 | 19 | 19 | 18 | 18 | 19 | 19 | 18 |
| $3M1C_4=$ | 2 | 2 | 2 | 2 | 2 | 2 | 2 | 2 |
| $T2C_5=$ | 13 | 12 | 12 | 12 | 12 | 12 | 12 | 13 |
| $C_2C_5=$ | 6 | 6 | 6 | 6 | 6 | 6 | 7 | 6 |
| $2M2C_4=$ | 59 | 59 | 59 | 60 | 60 | 58 | 58 | 59 |
| $C_6+$ Aromatics, Wt % | 42 | 27 | 17 | 9 | 9 | 9 | 6 | 5 |
| Liq. Prod. 90% Pt., °F.(D-2887) | 366 | 361 | 358 | 339 | 334 | 331 | 318 | 316 |

It should be immediately apparent that this experiment did not result in as good aging for the ZSM-5 zeolite in the second stage. This can be better seen by comparing the results obtained between Examples 3 and 4 at approximately the same time on stream. Comparisons will be made between Example 3 at 4.9 and 12.9 days and Example 4 at 4.7 days and 12.4 days, i.e. about 5 and about 13 days.

| | Example 3 | Example 4 |
|---|---|---|
| Hydrocarbon yield | | |
| about 5 days | 26.8 | 26.6 |
| about 13 days | 27.3 | 22.8 |
| CO Conversion | | |
| about 5 days | 96 | 92 |
| about 13 days | 96 | 82 |
| $H_2$ Conversions | | |
| about 5 days | 52 | 42 |
| about 13 days | 52 | 32 |
| Aromatics, % $C_6+$ | | |
| about 5 days | 26 | 9 |
| about 13 days | 20 | 5 |
| Olefins, % $C_5$ | | |
| about 5 days | 25 | 66 |
| about 13 days | 40 | 79 |

From the above, it is clearly demonstrated that the use of ZSM-5 in both stages results in enhanced performance.

What is claimed is:

1. In a process for converting synthesis gas comprising carbon monoxide and hydrogen to gasoline boiling components wherein synthesis gas is contracted in a first stage under conditions of elevated temperatures and pressure with a Fischer-Tropsch catalyst and the total product from said first stage contact is passed to a second stage containing an acidic crystalline zeolite having a pore diameter greater than about five Angstroms, a silica-to-alumina ratio of at least 12, a crystal density substantially below 1.6 grams per cubic centimeter and a constraint index of from 1 to 12 the improvement which comprises:

(a) carrying out said contact in said first stage at a temperature of 450°-750° F., a space velocity of 500-20,000 GHSV, and a pressure of from 50 to 1000 psig, with a catalyst composite comprising an intimate mixture of an iron or cobalt-containing Fischer-Tropsch component and a volume excess of a crystalline aluminosilicate zeolite having a pore size greater than 5 Angstroms, a silica-to-alumina ratio of at least 12 and a constraint index of from about 1 to 12, wherein the activity of said crystalline aluminosilicate zeolite in said first stage is balanced with said Fischer-Tropsch component so as to obtain products including a liquid olefinic naphtha having a boiling range of less than 400° F. at 90 percent overhead with an aromatic content of less than about 20 weight percent, an olefin plus aromatic content of at least 50 weight percent, wherein the olefins have predominantly branched chain double bonds;

(b) operating said second stage at a temperature of from 550° F. to about 800° F., a pressure of from 50 to about 1000 psig and at a gas hourly space velocity of from 500 to 20,000;

(c) recovering a $C_5+$ gasoline fraction in a yield of at least 40 weight percent based on the total hydrocarbons produced, said gasoline fraction having a boiling range of less than 400° F. at a 90 percent overhead and an aromatics content greater than 20 weight percent; and (d) producing methane plus ethane in an amount no greater than 30 weight percent.

2. The process of claim 1 with a crystalline aluminosilicate zeolite in both the first and second stage is ZSM-5.

3. The process of claim 2 wherein the ZSM-5 zeolite in the first stage is KZSM-5.

4. The process of claim 3 wherein a cobalt containing Fischer-Tropsch catalyst is used in the first stage and the temperature is from 470°-540° F.

5. The process of claim 3 wherein an iron containing Fischer-Tropsch catalyst is used in the first stage.

6. In a process for converting synthesis gas comprising carbon monoxide and hydrogen to gasoline boiling components wherein synthesis gas is contacted in a first stage under conditions of elevated temperatures and pressure with a Fischer-Tropsch catalyst and the total product from said first stage contact is passed to a second stage containing an acidic crystalline zeolite having a pore diameter greater than about five Angstroms, a silica-to-alumina ratio of at least 12, a crystal density substantially below 1.6 grams per cubic centimeter and a constraint index of from 1 to 12 the improvement which comprises:

(a) carrying out said contact in said first stage at a temperature of from 450°–750° F., a space velocity of 500–20,000 GHSV and a pressure from 50–1,000 psig with a catalyst composite comprising an intimate mixture of a potassium promoted iron Fischer-Tropsch component and a volume excess of a crystalline aluminosilicate zeolite having a pore size greater than five Angstroms, a silica-to-alumina ratio of at least 12 and a constraint index of from about 1 to 12, wherein the activity of said crystalline aluminosilicate zeolite in said first stage is balanced with said Fischer-Tropsch component so as to obtain products including a liquid olefinic naphtha having a boiling range of less than 400° F. at 90% overhead with an aromatic content of less than about 20 weight percent, an olefin plus aromatic content of at least 50 weight percent, wherein the olefins have predominantly branched chain double bonds;

(b) operating said second stage at a temperature of from 550° F. to about 800° F. a pressure of from 50 to about 1000 psig and at a gas hourly space velocity of from 500 to 20,000;

(c) recovering a $C_5+$ gasoline fraction in a yield of at least 40 weight percent based on the total hydrocarbons produced, said gasoline fraction having a boiling range of less than 400° F. at a 90% overhead and an aromatic content greater than 20 weight percent; and (d) producing methane plus ethane in an amount no greater than 30 weight percent.

7. The process of claim 6 wherein the catalyst in the first stage comprises an intimate mixture of potassium promoted iron and potassium ZSM-5 zeolite.

8. The process of claim 7 wherein the catalyst in the second stage is acid ZSM-5.

9. The process of claim 8 wherein the temperature of the first stage is 550°–700° F.

10. The process of claim 9 wherein the temperature of the second stage is from 550°–650° F.

* * * * *